(12) United States Patent
Jarvik

(10) Patent No.: US 9,636,441 B2
(45) Date of Patent: May 2, 2017

(54) SUPPORT STENT FOR TRANSVALVULAR CONDUIT

(71) Applicant: Robert Jarvik, New York, NY (US)

(72) Inventor: Robert Jarvik, New York, NY (US)

( * ) Notice: Subject to any disclaimer, the term of this patent is extended or adjusted under 35 U.S.C. 154(b) by 437 days.

(21) Appl. No.: 13/668,593

(22) Filed: Nov. 5, 2012

(65) Prior Publication Data
US 2014/0128967 A1 May 8, 2014

(51) Int. Cl.
| A61F 2/82 | (2013.01) |
| A61M 1/10 | (2006.01) |
| A61F 2/24 | (2006.01) |
| A61M 1/12 | (2006.01) |

(52) U.S. Cl.
CPC .............. *A61M 1/10* (2013.01); *A61F 2/2418* (2013.01); *A61F 2220/0041* (2013.01); *A61M 1/101* (2013.01); *A61M 1/122* (2014.02); *A61M 1/125* (2014.02)

(58) Field of Classification Search
CPC .................................... A61F 2/24; A61F 2/82
USPC ........................................................ 623/1.26
See application file for complete search history.

(56) References Cited

U.S. PATENT DOCUMENTS

| 4,919,647 A | 4/1990 | Nash |
| 2003/0040792 A1* | 2/2003 | Gabbay ........................ 623/2.11 |
| 2005/0148811 A1 | 7/2005 | Aboul-Hosn |
| 2010/0249489 A1 | 9/2010 | Jarvik |
| 2011/0124950 A1 | 5/2011 | Foster |
| 2011/0152999 A1 | 6/2011 | Hastings et al. |
| 2012/0059460 A1 | 3/2012 | Reitan |
| 2012/0310328 A1* | 12/2012 | Olson ........................ A61F 2/07 623/1.26 |

FOREIGN PATENT DOCUMENTS

EP 0445782 A1 9/1991

OTHER PUBLICATIONS

European Search Report Application No. 13191598.5 dated Apr. 3, 2014.

* cited by examiner

*Primary Examiner* — Matthew Schall
(74) *Attorney, Agent, or Firm* — Troutman Sanders LLP

(57) ABSTRACT

Miniature axial flow pumps are implanted inside the heart or major arteries to provide hemodynamic support. These pumps commonly utilize tubular blood conduit tubes to transport blood across the aortic valve. The valve leaflets themselves are very thin and flexible, and will seal against the conduit if it is centered within the valve orifice. If the conduit is not centered, a leaflet can be pushed to the side of the aorta, preventing the leaflets from sealing and providing a path for backflow. If the blood flow conduit remains pushed against the side of the valve for a long period of time, thrombus may form in the crevice between the conduit and the aorta, causing serious thromboembolic events such as stroke, if the thrombus breaks free. The present invention provides a conduit support device that retains the conduit centered within the annulus of the natural heart valve. A leaflet valve stent may be combined with a conduit support device comprised of a ring supported by posts attached to the valve stent ring. A blood pump may be attached to the center of a transvalvular support stent, for optimal fixation of the pump with relation to a trileaflet or bi-leaflet tissue or polymer valve.

5 Claims, 3 Drawing Sheets

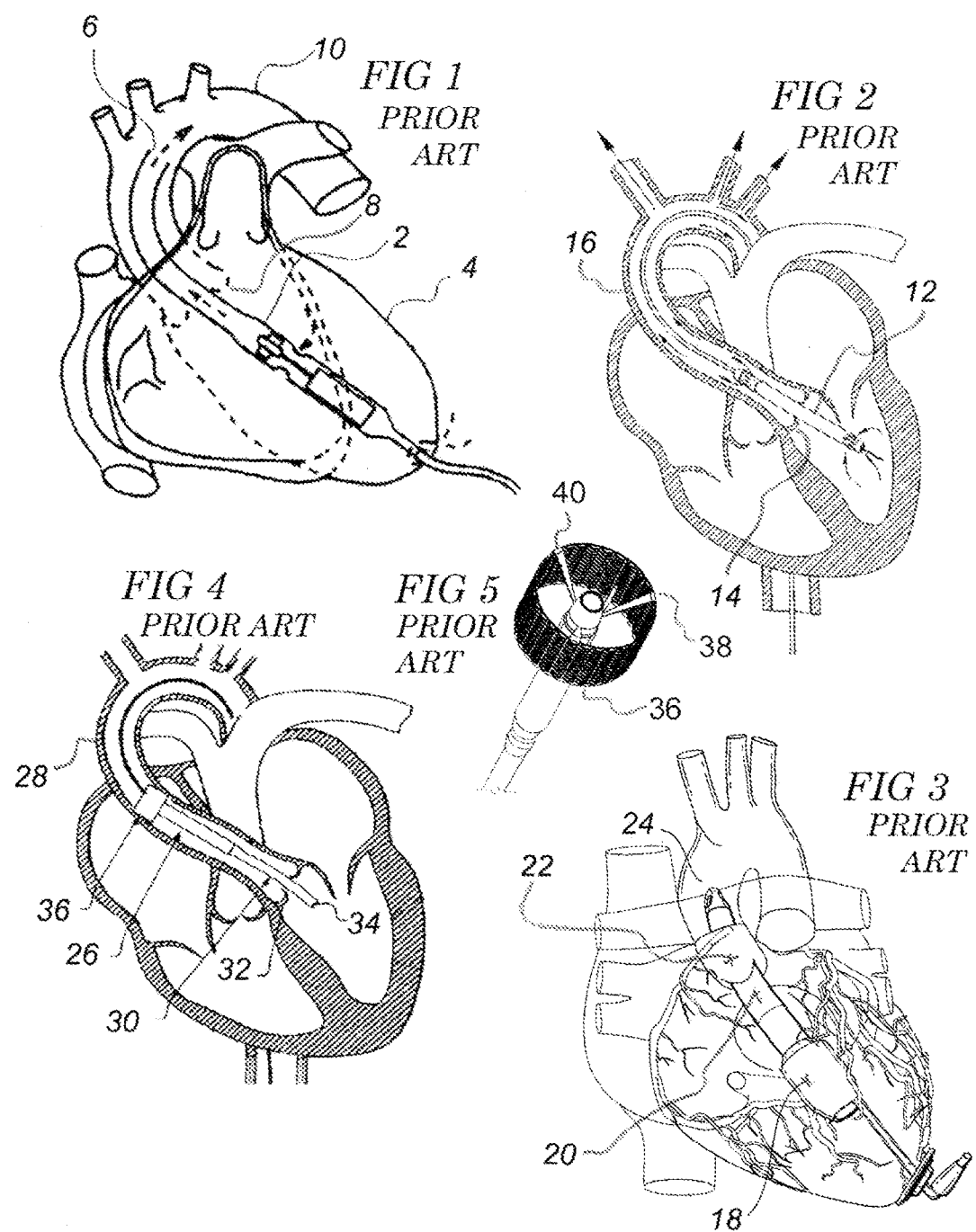

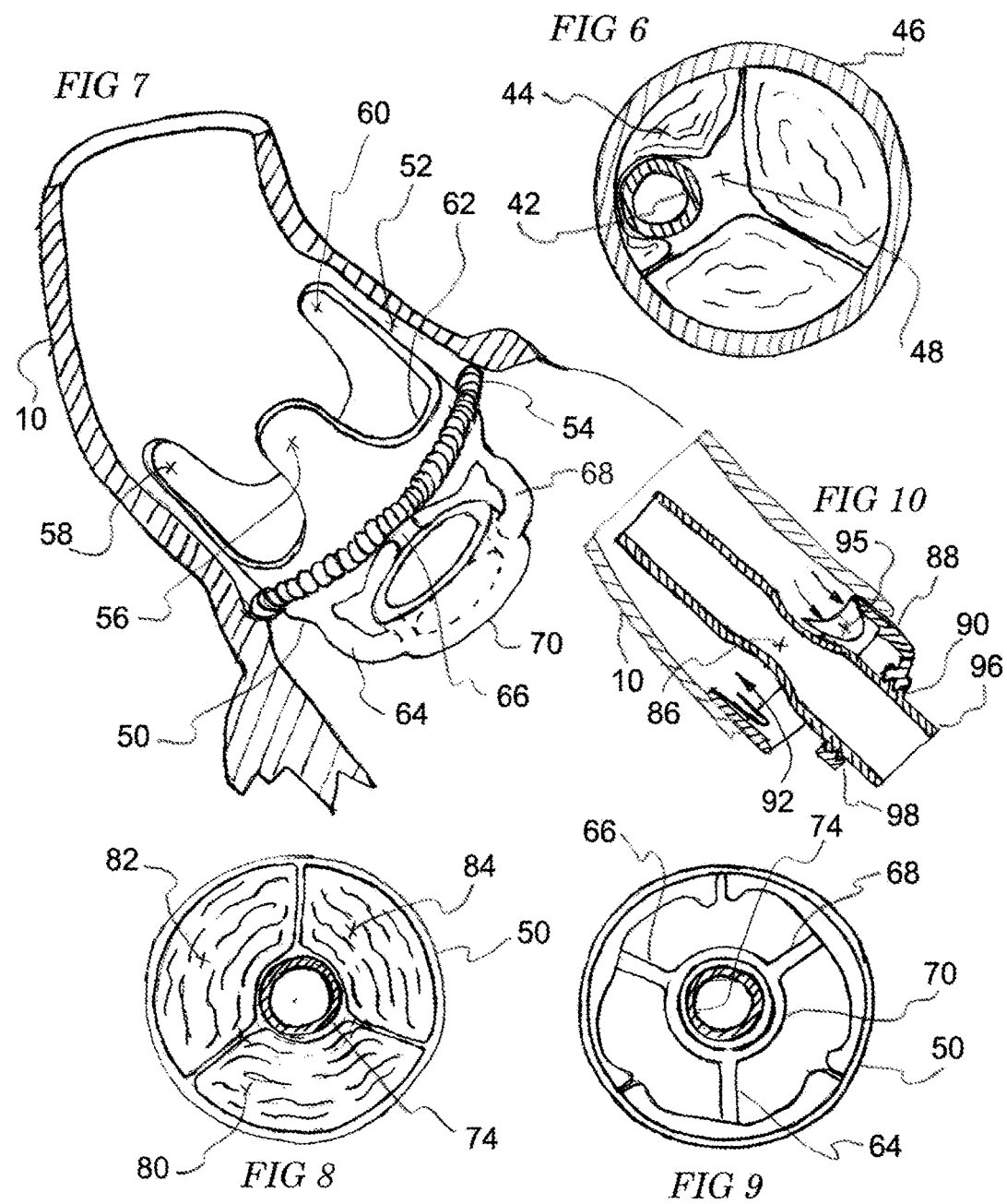

SUPPORT STENT FOR TRANSVALVULAR CONDUIT

BACKGROUND OF THE INVENTION

Small less invasive blood pumps are useful to augment the flow of patients in late stage heart failure. Early work with these devices included the hemopump U.S. Pat. No. 4,846,152, the Cannula pump U.S. Pat. Nos. 5,376,114, 5,755,784, 5,776,190, 5,888,241, and the HeartWare "long-horn" pump, US patent application No. 20090203957. Temporary axial flow blood pumps implanted for hours or days such as the Impella pump (Statorless intravascular microaxial flow pump U.S. Pat. No. 5,921,913, Intracardiac pump device U.S. Pat. No. 6,139,487 and others) are becoming widely applied. The Impella is presently FDA approved for use up to six hours. These devices all utilize small diameter tubes (conduits) through which blood transverses cardiac valves, most commonly the aortic valve. During systole the valve may open, with a portion of the flow ejected by the natural heart passing through the orifice between the leaflets, as well as part of the flow passing through the blood pump conduit. The position of the conduit with these devices is likely to be pushed towards one side of the valve and is not controlled to remain centered within the valve orifice. If the conduit is lodged in a position where it touches against the natural valve annulus, a crevice will be formed in which thrombus may form. If the conduit then moves, the thrombus could break free becoming a dangerous thromboembolis.

My previously patented valve pump U.S. Pat. No. 7,479,102 is directed to long term implant where the device can be implanted and remain functional for many years. Valve pumps are disclosed in which a very small pump is placed in the position of one of the leaflets of the aortic or pulmonic valve, leaving two of the three valve leaflets functional. The present invention provides means to hold a conduit or blood pump centered in the valve orifice, so that it will be optimally washed to prevent thrombus.

OBJECTS OF THE INVENTION

1. It is an object of the invention to provide a device to hold a blood flow conduit securely in place centered within the orifice of a leaflet heart valve.

2. It is a further object of the invention to stabilize a trans-valvular blood flow conduit in a central location within a leaflet type prosthetic heart valve such that the leaflets can open and close many millions of cycles without the valve wearing out or developing thrombus.

3. It is another object of the invention to improve the performance of miniature intravascular cardiac assist systems.

4. An additional object of the invention is to provide an improved trans-valvular blood pump fixation device for long term use.

5. A still further object of the invention is to provide a fixation device for trans-valvular conduits that will minimize the risk of thrombus formation by eliminating a crevice formed between the conduit and the side of the valve.

6. Additionally, it is an object of the invention to provide a device to maintain patency of a trans-valvular conduit within a leaflet valve and the valve itself, free of thrombus with minimal or no antigoagulation needed.

7. Another object of the invention is to provide a valved trans-valvular conduit retention device that mates with a miniature trans-valvular blood pump, and retains the pump in the optimal position with relation to a conduit portion of the pump that transverses the valve.

8. It is a further object of the invention to provide a valved trans-valvular conduit retention device incorporating tissue valve leaflets that may be wet stored in sterile condition, and at surgery, used with a dry sterilized conduit or blood pump.

THE DRAWINGS

FIG. 1 is a drawing from prior art U.S. Pat. No. 5,376,114 showing a blood pump positioned within the left ventricle and a blood flow conduit passing through the aortic valve.

FIG. 2 is a drawing from prior art U.S. Pat. No. 7,022,100 showing a blood pump positioned partly within the left ventricle and partly within the aorta and having a blood flow conduit that transverses the aortic valve.

FIG. 3 is a prior art drawing from US patent application No. 20090203957 showing a blood pump located within the left ventricle, having a blood flow conduit passing across the aortic valve, and having a fixation device located at the left ventricular apex.

FIG. 4 is a prior art drawing from US patent application No. 20120029265 showing a blood pump located within the aorta and having a blood flow conduit passing across the aortic valve, and having a fixation device located within the aorta.

FIG. 5 is a drawing from prior art patent application No. 20120029265 showing a fixation device that includes an expandable mesh stent and hinged support arms.

FIG. 6 is a view of an aorta and aortic valve leaflets showing a transvalvular conduit in a non-centered position that pushes one valve leaflet to the side.

FIG. 7 is an illustration of an embodiment of the present invention including a valve stent and conduit support ring in the position within the aortic annulus where it is affixed by suturing its sewing cuff to the aorta.

FIG. 8 is an illustration of a transvalvular conduit located centrally within three aortic valve leaflets showing the leaflets closed against the conduit.

FIG. 9 is an illustration of an embodiment of the present invention having a support ring maintained in a central position by three posts, and supporting a blood flow conduit within the support ring. The three valve leaflets are shown in the open position.

FIG. 10 is a longitudinal section of a transvalvular conduit secured to a valve stent mounted central support ring by means of screw threads.

SPECIFIC DESCRIPTION OF THE INVENTION

Figure 11:
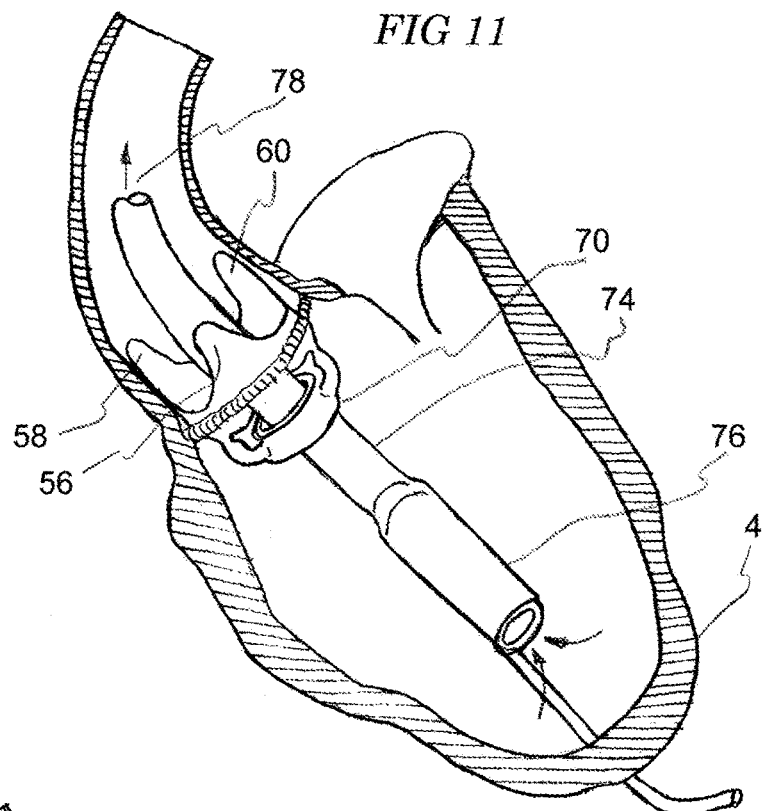
FIG. 11 is an illustration of a transvalvular blood flow conduit held in the center of the aortic annulus by an embodiment of the present invention. An intraventricular blood pump receives blood inflow within the left ventricle, and pumps the blood through the center of the aortic valve via the conduit, and then expels the blood into the aorta.

Miniature blood pumps have been developed that may be implanted surgically, such as via an incision in the left ventricular apex, and others have been developed that may be implanted in the cath lab, via a peripheral vessel such as the femoral artery. A number of these utilize a conduit passed across the aortic valve through which the blood pumped by the device must pass. Referring to FIG. 1, blood pump 2 has its blood inflow within the left ventricle 4, and uses a conduit 6 to channel blood across the aortic valve 8, into the aorta 10. FIG. 2 shows a blood pump 12 located partly in the left ventricle and partly in the aorta, that includes a conduit through which blood flows across the aortic valve 14 and into the aorta 16.

FIG. 3 shows a blood pump 18, utilizing an outflow conduit 20 to convey blood across aortic valve 22 into the aorta 24. In FIG. 4, a blood pump 26 is located in the aorta 28, and uses an inflow conduit 30 that passes across the aortic valve 32 and has an inlet opening 34 within the left ventricle. FIG. 5 is an enlarged view of an expandable mesh fixation device 36 that holds the blood pump centered in the aorta using posts 38, 40 at a position separated from the aortic valve. The function of this fixation device is to retain the pump in position so that the pump and inflow conduit will not shift position due to the reactive force of the blood jetting into the aorta.

With small blood pumps that use conduits passing across the aortic valve, if the conduit is maintained centrally within the valve the leaflets seal against it without regurgitation. If the conduit is small in diameter, which limits the blood flow to relatively low values, it may locate between leaflets and seal with little regurgitation. But if the conduit is large enough to provide flow above 2-3 L/min, unless it is retained centered in the valve, it can push valve leaflets against one side of the aorta and prevent the valve from closing effectively.

Referring to FIG. 6, a blood flow conduit 42 compresses one valve leaflet 44 against the aortic wall 46. This prevents the three leaflets from sealing against each other, and creates an opening 48 where regurgitant flow occurs. The present invention provides a support structure that holds the conduit centered within the valve leaflets which seal against the conduit as shown in FIG. 8, thus avoiding regurgitant flow.

Referring to FIG. 7, a support stent 50 is shown within the aortic annulus 52 retained by a sewing cuff 54. In this illustration, for clarity, the three valve leaflet support struts 56, 58, 60 are shown without valve leaflets attached. These three struts are joined to one another by a integral ring 62. Note that the struts project in the direction defined from the left ventricular apex towards the aorta. The struts actually project into the aorta. Affixed to the ring 62, are three support posts 64, 66, 68 that attach to a centrally located conduit support ring 70. The leaflet support struts, conduit support ring posts, and conduit support ring are all preferably machined out of a solid bar of polymer, such as homopolymer acetal, or may be molded as one piece. Note that the valve leaflet support struts are located in the aorta 10, and that the conduit support ring posts and conduit support ring are within the outflow tract of the left ventricle close to the annulus of the aortic valve 52.

Various types of tissue valves are known in the prior art that utilize stents of differing design to support the leaflets. Porcine valve leaflets may be used, pericardial tissue has been used to fashion leaflets, and polymer leaflets have also been developed. The present invention provides a leaflet support stent combined with a conduit support structure which may be a ring 70, or simply the ends of three posts 64, 66, 68 without using a ring. If the ends of the posts are used to hold the conduit centered, the diameter of the conduit must fit closely within the posts so that it is well retained. The device also includes a sewing cuff 54 that is used to suture the valve and conduit support into the aorta using surgical techniques that have been widely used for aortic valve replacements. Referring to FIG. 11, it is clearly seen that a blood flow conduit 74 conducts blood flow produced by blood pump 76 from the left ventricle (arrows), through the center of the valve support ring 70, and into the aorta at the end of the conduit 78.

As best seen in FIG. 9 with the valve leaflets open, the conduit 74 is held in the center of the valve between the leaflets 80, 82, 84, by ring 70 which is supported by posts 64, 66, 68. The posts, in turn, are held by the stent support ring 50 that is sutured into the aorta by sewing ring 72.

FIG. 10 illustrates an embodiment where the conduit includes a narrowed diameter 86 where it passes through the center of the valve leaflets. In this drawing, one leaflet is shown open with flow passing through indicated by the single arrow 92, and another leaflet is shown in the closed position with two arrows 94 indicating pressure within the aorta that closes the leaflet 95 against the narrowed portion of the conduit. In actual conditions the three leaflets open and close almost simultaneously, so the illustration is representative of the two positions (open and closed) but does not represent the configuration of the valve at one point in time. If the conduit includes a narrowed portion where the leaflets are intended to close, some way to retain the conduit in the correct axial position is needed. In the embodiment shown in FIG. 10 the conduit 96 is retained by an internally threaded ring 90 attached to the valve stents by post 88. The conduit includes external threads 98 that secure it to the threaded ring. This locks the conduit in the correct axial position such that the narrowed lumen 86 is properly aligned axially with the valve leaflets.

Figure 12:
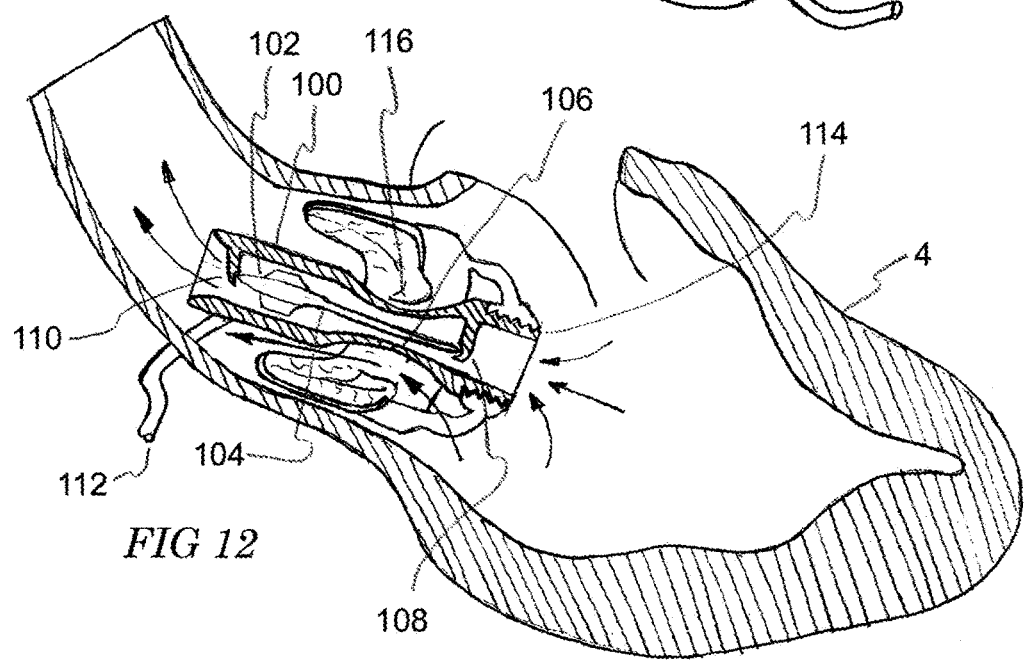
FIG. 12 is an embodiment of the present invention including a threaded support ring adapted to mount a transvalvular blood pump to the support ring.

The transvalvular conduit support stent may be configured to directly mount a blood pump by means of a threaded connection 114 or other direct attachment mechanisms. Referring to FIG. 12, a blood pump 100 includes an impeller 102 mounted on a rotor having a small diameter elongated shaft 104 that passes through the center of a narrowed portion of a transvalvular conduit 106 formed integral with the blood pump. Inflow side and outflow side rotor bearings 108, 110 support the pump rotor within an electric motor (not shown) that powers it via electric cable 112. The position of the threads 114 that connect the pump to the support ring of the stent is such that the valve leaflets close against the narrowed part of the blood pump conduit as seen at 116. Note that this illustration, similar to FIG. 10, shows one leaflet open and one closed to illustrate both of these positions.

With this embodiment of the invention, the transvalvular support stent is first sutured into the aortic annulus in essentially the same way as an aortic tissue valve implant would be done. Next, the blood pump, which is a separate device, is screwed into the threaded support ring. This is done prior to passing the power cable across the aortic wall (as shown in FIG. 12). After the pump is attached, the power cable is passed across a hole in the aortic wall and fastened in place. In this position, the cable prevents the pump from becoming unscrewed because the cable locks it in place rotationally.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. A valved conduit support comprising:
a transvalvular blood flow conduit;
a first ring adapted to hold said transvalvular conduit passing therethrough in a centered position, said conduit support having two or three cardiac valve leaflets affixed to an annular stent, said conduit support comprising:
a circular or oval ring with two or three valve leaflet support members affixed thereto that project axially away from the plane of said circular ring or oval in the direction of flow through the valve, and
one or more conduit support posts also affixed to said circular ring that project axially in the direction opposite to the direction of blood flow through said valve, wherein said transvalvular conduit also passes through the leaflets and said circular or oval ring.

2. The valved support of claim 1 further comprising a threaded support affixed to said posts in an axial position that permits valve leaflets affixed to said leaflet support members to seal against the surface of said transvalvular conduit in an optimal predetermined axial position by means of a threaded member interconnected to said transvalvular conduit.

3. The valved support of claim 2 in which the transvalvular conduit is a portion of a blood pump that transverses a heart valve.

4. The valved support of claim 2 in which the transvalvular conduit is connected to a blood pump positioned in the aorta or pulmonary artery.

5. The valved support of claim 2 in which the transvalvular conduit is connected to a blood pump positioned in the left or right ventricle.

* * * * *